United States Patent [19]

Proto et al.

[11] Patent Number: 5,168,619
[45] Date of Patent: Dec. 8, 1992

[54] METHOD FOR ATTACHING SURGICAL SUTURE COMPONENTS

[75] Inventors: George R. Proto, West Haven; Francis D. Colligan, Waterbury, both of Conn.

[73] Assignee: United States Surgical Corporation, Norwalk, Conn.

[21] Appl. No.: 712,688

[22] Filed: Jun. 10, 1991

Related U.S. Application Data

[62] Division of Ser. No. 431,306, Nov. 3, 1989, Pat. No. 5,099,676.

[51] Int. Cl.$^5$ ..................... B21D 39/00; B23P 11/02
[52] U.S. Cl. ....................................... 29/508; 29/517
[58] Field of Search ............... 29/508, 515, 516, 517, 29/518; 72/360, 416; 163/1, 6; 604/272, 273

[56] References Cited

U.S. PATENT DOCUMENTS

| | | |
|---|---|---|
| Re. 27,735 | 8/1973 | Shave et al. . |
| Re. 31,084 | 11/1982 | Birks . |
| 1,558,037 | 10/1925 | Morton . |
| 1,578,543 | 3/1926 | Montgomery . |
| 2,067,568 | 1/1937 | Grunthal . |
| 2,205,893 | 6/1940 | Unger . |
| 2,411,079 | 11/1946 | Baule . |
| 2,620,028 | 12/1952 | Kohut . |
| 2,958,929 | 11/1960 | Vineberg et al. . |
| 2,983,898 | 5/1961 | Kalmar et al. . |
| 3,055,412 | 9/1962 | Dibner . |
| 3,130,489 | 4/1964 | Schlage . |
| 3,251,216 | 5/1966 | Broske . |
| 3,253,328 | 5/1966 | Baldwin . |
| 3,365,927 | 1/1968 | Lynch . |
| 3,643,327 | 2/1972 | Jackson . |
| 3,771,343 | 11/1973 | Dawson . |
| 3,890,975 | 6/1975 | McGregor . |
| 3,910,282 | 10/1975 | Messer et al. . |
| 3,963,031 | 6/1976 | Hunter . |
| 3,972,219 | 8/1976 | Riehl . |
| 3,980,177 | 9/1976 | McGregor . |
| 4,054,144 | 10/1977 | Hoffman et al. . |
| 4,060,885 | 12/1977 | Hoffman et al. . |
| 4,067,224 | 1/1978 | Birks . |
| 4,072,041 | 2/1978 | Hoffman et al. . |
| 4,192,171 | 3/1980 | Hamilton . |
| 4,292,833 | 10/1981 | Lapp . |
| 4,361,948 | 12/1982 | Omata . |
| 4,498,222 | 2/1985 | Ono et al. . |
| 4,567,650 | 2/1986 | Balyasny et al. . |
| 4,719,789 | 1/1988 | Wiebe et al. . |
| 4,722,384 | 2/1988 | Matsutani . |
| 4,799,311 | 1/1989 | Matsutani . |

FOREIGN PATENT DOCUMENTS

| | | |
|---|---|---|
| 0249504 | 12/1987 | European Pat. Off. . |
| 8715099 | 3/1988 | Fed. Rep. of Germany . |
| 1526222 | 9/1978 | United Kingdom . |

Primary Examiner—Timothy V. Eley
Attorney, Agent, or Firm—Thomas R. Bremer; Peter G. Dilworth; Rocco S. Barrese

[57] ABSTRACT

An apparatus is disclosed for attaching a surgical needle having a generally cylindrical end portin defining an elongated aperture having a generally circular cross-section and a suture having a generally elongated end portion of generally circular cross-section corresponding in dimension to the elongated aperture of the needle. The apparatus includes a pair of dies, each having a generally arcuate surface portion having irregularities including concave portions such that when the cylindrical end portion of the suture is positioned within the aperture of the needle and the dies are positioned about the generally cylindrical end portion of the needle with the surface portions facing the outer surface thereof, the application of inward force to the dies causes the dies to impact the needle and produces inward crimping of the needle so as to attach the needle to the suture. The concave portions define material relief zones to receive and collect deformed material from the needle so as to avoid distortion of the needle. According to the invention, the symmetry of the needle is maintained and the attachment is predictable and superior to those of the prior art. A method of forming such attachment is also disclosed.

19 Claims, 3 Drawing Sheets

METHOD FOR ATTACHING SURGICAL SUTURE COMPONENTS

This is a divisional of copending application Ser. No. 07/431,306 filed Nov. 3, 1989 now U.S. Pat. No. 5,099,676.

BACKGROUND OF THE INVENTION

1. Field of the Invention

The present invention relates to surgical sutures and their production. In particular, the invention relates to surgical sutures and apparatus for the attachment of surgical needles to surgical sutures.

2. Description of Related Art

In the past, surgical needles with an eye for reception of the suture have been used. As in conventional sewing, the thread is sometimes doubled through the eye of the needle. The doubled end of the thread in the eye must pass through tissues during use, which enlarges the opening made in the tissue. This leads to loss of tightness and increased trauma. Because of this problem, there has been a trend towards eyeless needles in which the end of the suture is attached to the needle so that the suture is pulled through the tissue thus minimizing the opening and causing a minimum of trauma.

The most common surgical suture of this type is a single-use needle of appropriate size and shape which is crimped to the end of the suture, so that the needle is used once and then discarded. The attachment can be accomplished by use of a "drilled end" needle; that is, one in which a concentric aperture is formed in the end of the needle in which the suture is placed and the needle crimped around the suture. Alternatively, a "flanged" needle may be utilized in which a U-shaped channel is stamped into the end of the needle with the ends of the "U" being crimped about the suture to hold the suture together.

The attachment must be one which is: predictably secure; causes a minimum of damage to tissue; is convenient for the using surgeon; permits sterilization; and entails reasonable costs. In addition, the attachment must withstand the rigors of manufacture, sterilization, storage, shipment and use.

During use, it has been found that upon completion of the stitching procedure by the surgeon, it is convenient for the surgeon to be able to readily detach the needle from the suture thus permitting the end of the suture to be tied or otherwise secured. The needle may thereafter be removed from the work area so as to avoid harm to the patient, surgeon and other personnel. Cutting the suture with scissors or a scalpel is a convenient method of disengaging the needle but requires an extra instrument and an extra manipulation.

More recently, techniques have been developed to attach the suture to the needle in a manner which permits the surgeon to readily separate the components by merely tugging at the needle at the end of the stitching procedure.

The pull required for tugging the needle from the suture is referred to in the U.S. Pharmacopeia as "needle-attachment" or "testing the security of attachment of eyeless needles" to sutures. For convenience, the term "pull-out" is used.

Experience and testing procedures have determined that the pull-out must be at a sufficiently high value that the suture may be placed without risk of the needle becoming detached from the suture during placement; and yet it must pull-out at a value far below the breaking strength of the suture and will predictably pull-out before the suture breaks. In addition, the suture must pull-out at a value which is reasonably exertable upon the needle by the surgeon at the time of use.

Conventional crimp operations are difficult to control. Usually a crimp is created between several dies which close to a fixed gap. Any variation in: the crimping dies, the needle size, the hole size, or the suture size alters the degree of crimp. However, with such techniques, the variation can be larger than is acceptable in the manufacture of controlled release or controlled pull-out sutures.

The conventional crimping method requires that the back end of the needle be struck with two half moon shaped dies. The needle is then rotated 90° and the dies are arranged to strike the needle a second time. In effect, the first strike changes a round hole into one of eliptical shape, i.e., major and minor axes. The act of rotating the needle 90° and repeating the operation to some extent, causes the minor axis to become its counterpart, and the major axis to become the minor axis thereby completing the attachment in a relatively uniform manner. The effect of this procedure is to distort the end of the needle thereby causing it to lose its symmetry. This last mentioned disadvantage results in corresponding asymmetry of tissue apertures during use.

The diameter of the suture, the diameter of the needle, the concentricity of the aperture in the needle, the outside diameter of the needle, the braid size of the suture, coating material, time and concentration of baths, and drying conditions are all extremely critical in predicting and controlling the pull-out force. In addition to size effects, the surface smoothness of the suture and the needle aperture, and lubricants on either components affect the pull-out values. The conventional method of crimping, as described, underscores many of these parametric inconsistencies and necessarily utilizes multiple hits to overcome these process variabilities.

To date, techniques devised for connecting such suture components in a manner to perform within the preferred guidelines are not effective in maintaining needle symmetry and uniformity of dimensions, particularly with a single hit. The present invention avoids the aforementioned disadvantages and provides a die and a method for attaching surgical sutures to needles in a controlled manner while retaining the symmetry of the needle, all with less time and expense.

SUMMARY OF THE INVENTION

The present invention relates to a novel clover leaf die for attaching the components of surgical sutures which avoids the aforementioned disadvantages of known techniques while providing suture connections which perform within the desired predetermined parameters. Almost perfect symmetry of the attaching suture needle is maintained.

The novel clover leaf dies are used to attach a suture either in the form of a braid or monofilament, to a drilled end needle. The die is typically used in a suture attaching machine to attach a suture to a drilled end surgical needle.

The novel clover leaf die provides a better method of crimping surgical needles to sutures. The novel clover leaf shape provides a more uniform and quicker swage than obtainable using conventional attaching dies.

The invention provides two very significant improvements when compared to conventional dies. A single hit instead of two or more is used to develop the compression or swage forces while a uniquely defined irregular shape having concavities for reception of swaged material is provided. This feature improves the manufacturing economics and reliability of the attaching process. Test reports confirm that predictable pull-out forces are achieved in a convenient and controlled manner using the novel clover leaf shape dies of the present invention. Further, the needle symmetry is maintained in a much improved fashion. The improved needle symmetry is a benefit to the surgeon and the manufacturer.

In a broader sense, the invention relates to an apparatus for attaching two members, at least a first member having a generally arcuate outer surface portion and defining an elongated aperture of generally arcuate cross-section, and a second member including at least an end portion of generally arcuate outer configuration corresponding in configuration and dimension to the elongated aperture of the first member. The apparatus comprises a pair of dies each having an irregular surface portion corresponding to the arcuate outer surface portion of the first member and including generally inwardly extending crimping portions spaced by a plurality of concavities defining material relief zones. When the end portion of the second member is positioned within the aperture of the first member and the dies are positioned about the corresponding portion of the first member with the irregular surfaces facing the first member, and impact energy is applied to displace the dies toward each other, the inwardly extending crimping surfaces of each die engages the first member and transmits inward forces thereto so as to attach the members, while portions of material forming part of the first member adjacent thereto and stricken by the inwardly extending crimping portions are permitted to be deformed and to collect within adjacent relief zones defined by the concavities.

In particular, an apparatus is disclosed for crimping a cylindrical member for attachment to an elongated member of circular cross-section of dimension similar to the inner dimension of the cylindrical member. A pair of dies each has a generally arcuate undulating surface portion including concave portions such that when at least an end portion of the second member is positioned within the aperture of the first member and the dies are positioned about the corresponding outer portion of the first member, the application of force to the dies toward each other causes the surface portions of the dies to engage the first member and transmit inward crimping forces thereto so as to attach the members. The concave portions define relief zones which permit deformed material of the first member to collect therein so as to avoid distortion of the first member.

In the preferred embodiment the apparatus is utilized for attaching a surgical needle having a generally cylindrical end portion defining an elongated aperture having a generally circular cross-section and a suture having a generally elongated end portion of generally circular cross-section corresponding in dimension to the elongated aperture of the needle. The dies are adapted for attaching a surgical needle to a surgical suture made of at least one of suture materials such as silk, nylon, linen, cotton, polyester, polypropylene, stainless steel, natural materials such as catgut, and synthetic polymers having glycolic acid ester linkages subject to hydrolytic degradation to non-toxic, tissue compatible absorbable components, including polyglycolic acid. The surgical suture is made from a material which is braided, twisted or monofilament. The needle is typically of stainless steel of the drilled end type. Typically, the swaging dies are preferably of a hardened material such as tungsten carbide, and high speed steels.

A method is also disclosed for attaching a surgical needle having a generally cylindrical outer end portion and defining an elongated aperture having a generally circular cross-section, and a suture having a generally elongated end portion of generally circular cross-section corresponding in dimension to the elongated aperture of the needle, which comprises configuring a pair of dies such that each has a generally arcuate surface portion having irregularities including concave portions, positioning an end portion of the suture within the aperture of the needle, positioning the pair of dies adjacent the corresponding cylindrical portion of the needle with the surface portions facing the generally cylindrical outer end portion of the needle, applying inward force to the dies to displace the dies toward each other causing the dies to engage the needle so as to cause the generally arcuate portion to engage the surface portion of the needle to thereby cause crimping of the needle and reduction of the average dimension of the aperture defined thereby, whereby the concave portions define material relief zones to receive and collect deformed material from the needle thereby avoiding distortion of the needle.

Preferably the step of configuring the pair of dies comprises configuring the arcuate surface portion so as to have continuous undulations defined by alternating convexities and concavities. At least the portions of the dies defining the generally arcuate surface portion is comprised of hardened material, preferably is tungsten carbide.

According to the method of the invention, the needle may be detachably attached to the suture so as to be readily separated as mentioned, by a quick tug provided by the surgeon. Alternatively, the needle may be attached with greater pull-out to provide a "non-detachable" suture, in which case the suture may be separated from the needle in a more conventional manner, as by cutting the scissors or scalpel.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
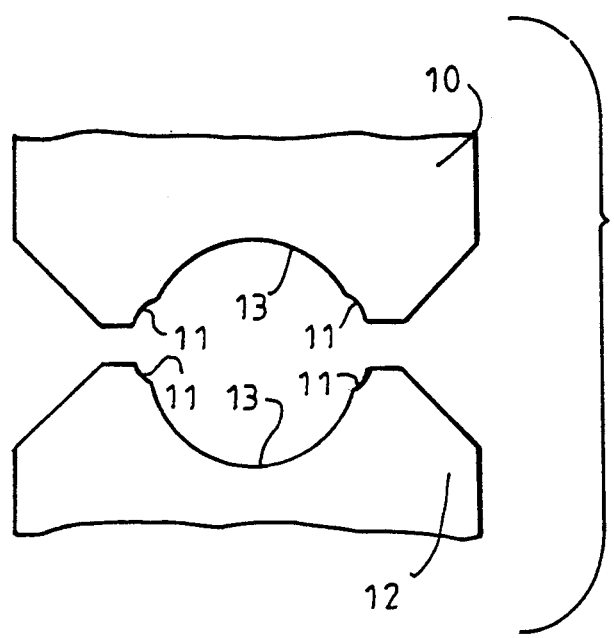
FIG. 1 is a plan view of a pair of conventional lap-overlap, semi-circular shaped dies.

Referring initially to FIG. 1 there is illustrated a pair of conventional "lap-overlap" dies 10, 12 of the known type utilized to attach a suture to a surgical needle. The working surfaces of the dies are shown at 13 and are each generally semi-circular in shape and include overlap regions 11 to receive limited amounts of excess material overflowing during the crimping process. The working surface of each die 10 shown at 13 is a "lap" region and has adjacent arcuate inner portions 11—designated as "overlap" regions—to receive limited amounts of excess needle material overflowing during the crimping process. The overlap regions are of lesser radii than the lap region and are not concentric as shown. The lap region is configured and dimensioned to receive the elongated apertured rear end portion of a surgical needle between them.

To attach a needle to a suture, the dies are positioned within an apparatus as will be described hereinbelow. The apparatus is arranged to cause both dies to simultaneously move toward each other and strike the needle while it is positioned between them. This causes the needle to become elliptical in cross-section by portions of metal deforming into regions 11. This process reduces the average cross-sectional dimension of the opening. Once the dies are impacted toward each other, they are separated and the needle is rotated 90°. The dies are then struck once again and the attachment is completed. In essence, the first strike causes the circular aperture in the needle to become elliptical. The second strike completes the attachment and reverses the distortion imparted to the needle. In certain instances additional hits are required to secure the suture to the needle. This procedure necessitates at least a dual step attachment which in turn requires substantial time and labor. As noted previously, attachments made according to this procedure are not always satisfactory for several reasons such as strength of the attachment, asymmetry of the needle, etc. In such cases, the suture must be discarded. In some instances, multiple hits greater than two are required to attach the suture to the needle. This procedure necessitates additional time and labor.

Figure 2:
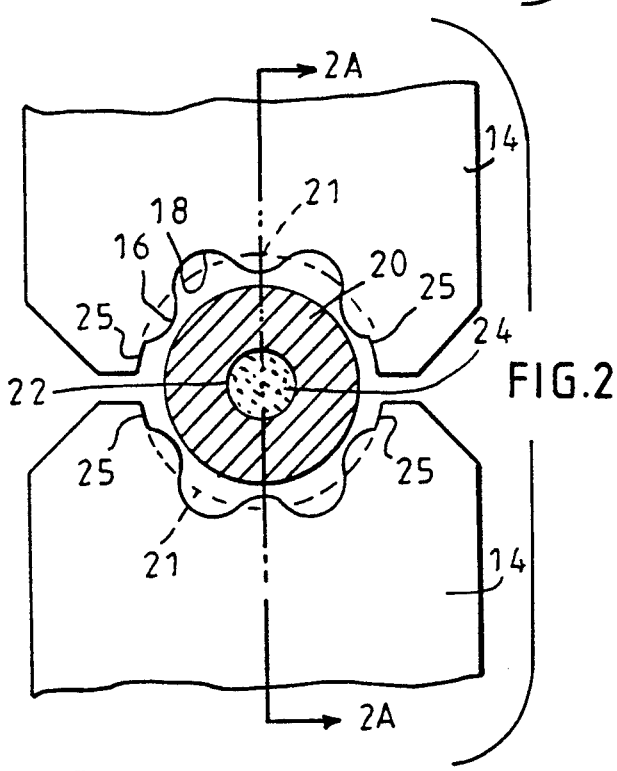
FIG. 2 is a plan view of a pair of clover leaf swaging dies according to the present invention with a needle and suture positioned therebetween for attachment to each other.
Figure 2A:
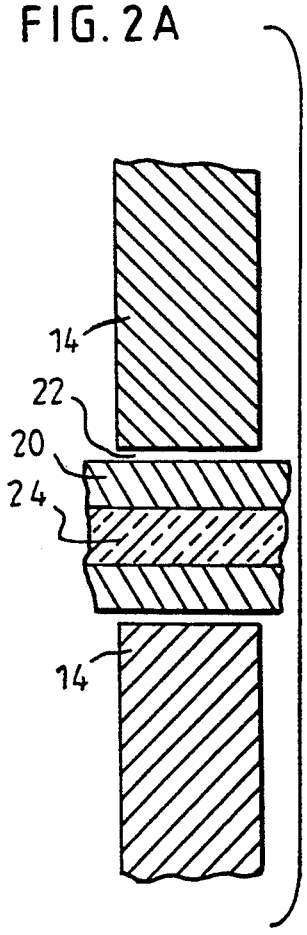
FIG. 2A is a cross-sectional view taken along lines 2A—2A of FIG. 2.

Referring now to FIG. 2, a pair of dies 14 constructed according to the present invention is disclosed. As can be seen each die 14 is identical to the other and in plan view, has a clover leaf shape which is defined by a generally circular surface having a series of interconnected alternating individual convex and concave curved surfaces. The convex surfaces are shown at 16 and the concave surfaces are shown at 18. Each has a radius generally less than the radius of the primary circular curve, i.e an imaginary "mean" circle which is shown in dotted lines 21. End portions 25 are preferably shaped as arcuate continuations of the "mean" circle as shown. Each die is shown in position prior to impact on a suture needle 20 having an aperture 22 in which the end portion of suture 24 is positioned. During the crimping process, the alternating individual convex and concave curved portions 16, 18 allow needle material swaged by the crimping action to flow from the convex to the concave areas and to collect therein thus avoiding the previously known deleterious distortion effect of prior art dies. In essence, the die converts a single inwardly directed impact into a complex combination of radial and circumferential forces which in turn provide a combination of crimping and swaging forces which attach the needle 20 to the suture 24. The actual crimping action is provided by the convexities 16 and the swaged material reception and collection is provided by the concavities 18.

Figure 3:
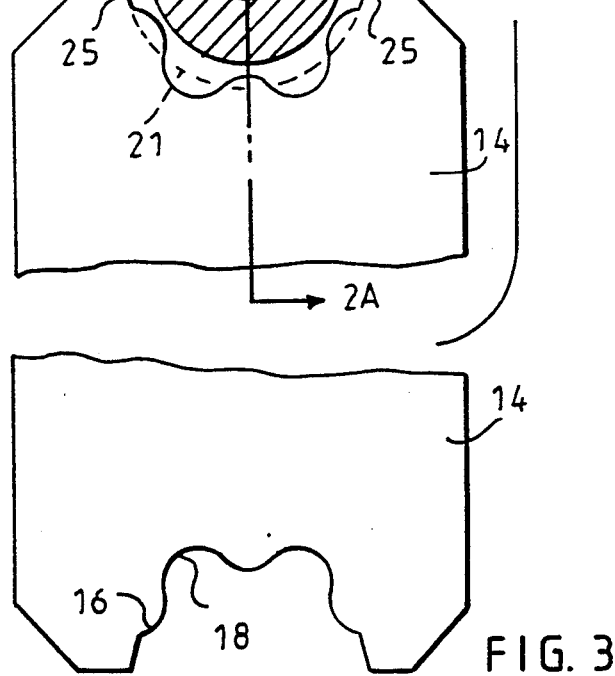
FIG. 3 is an enlarged plan view of a portion of one of the clover leaf dies of FIG. 2.

Thus it can be seen that the transformation of a single inward radial force on the clover leaf dies shown in FIGS. 2-3 not only provides unique attachment of the suture components, but also maintains the symmetry of the final work product by providing 1) symmetrical inward forces; 2) concave portions for collection of superfluous material distorted or swaged out of position by the attachment; and 3) relatively minor surface distortion.

Figure 4:
FIG. 4 is a photomicrograph of an end view of a needle with portions of sutures removed illustrating the effects of the crimping attachment accomplished by a pair of clover leaf dies according to the present invention.
Figure 5:
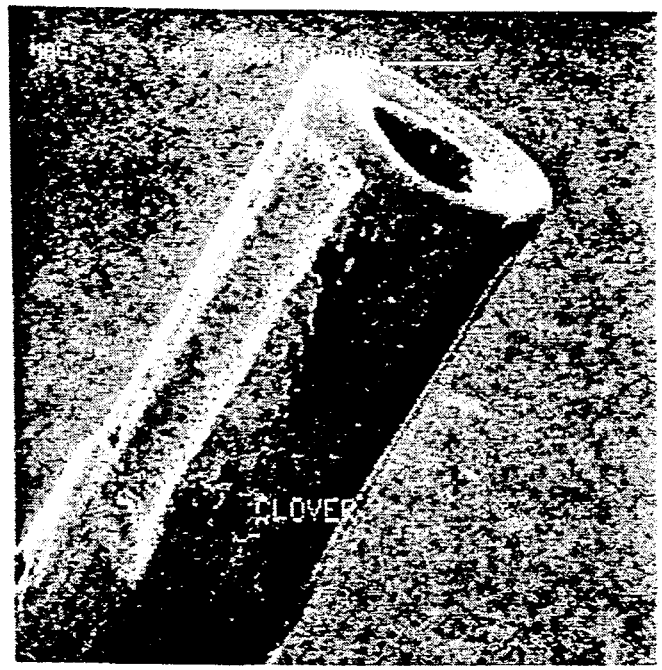
FIG. 5 is a photomicrograph illustrating a perspective view of the "crimped" needle shown in FIG. 4, and the effects of the dies of the present invention on the surface of the needle.

Referring now to FIGS. 4 and 5, the photomicrographs illustrate the needle after the crimping process. The swaged material distorts and collects about the needle in the areas defined by the concavities 18 of the dies 14. This is the result of the complex combination of inward crimping forces and the inward and circumferential swaging forces resulting from a single inward impact force on the dies. As can be seen, the surface of the needle as shown in FIG. 5 includes alternating concavities and convexities corresponding to the shape of the needle and the dies, while maintaining the general asymmetry of the needle.

Figure 6:
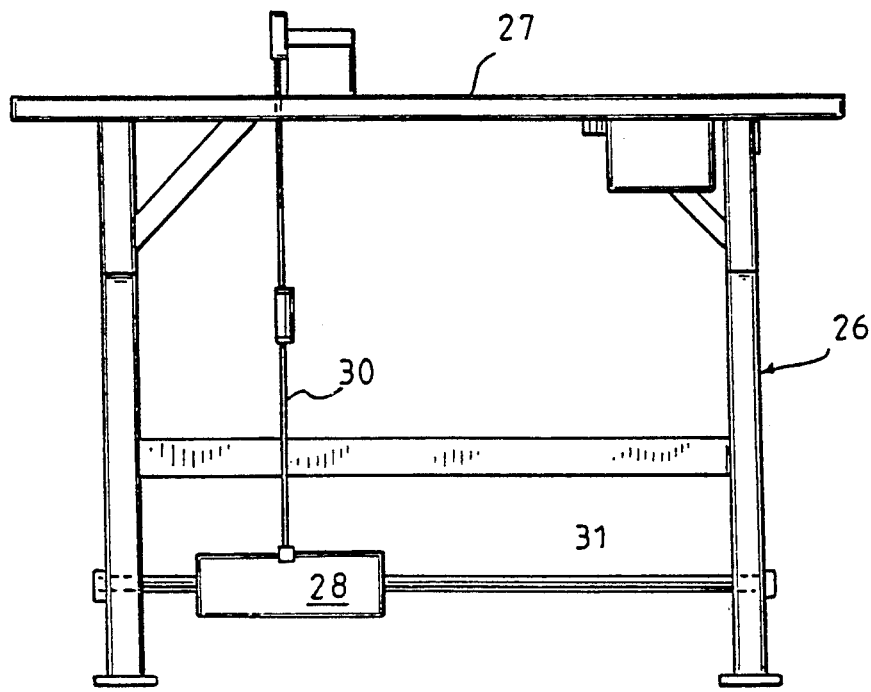
FIG. 6 is a front view of an apparatus with which the clover leaf dies according to the present invention may be utilized to attach a suture to a needle by crimping.
Figure 7A:
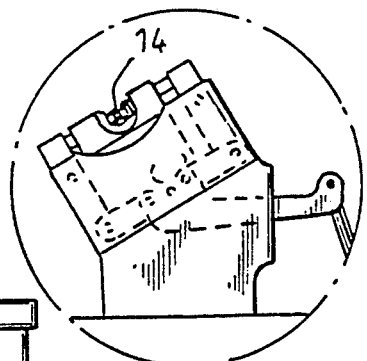
FIG. 7A is an exploded view illustrating the clover leaf dies of the present invention mounted in the apparatus of FIG. 7 for attaching a suture to a needle.
Figure 7:
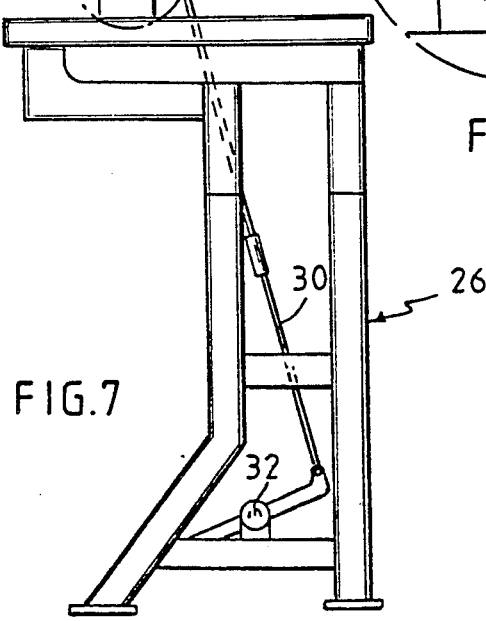
FIG. 7 is a side view of the apparatus shown in FIG. 6.

Referring now to FIGS. 6 and 7 there is shown an exemplary apparatus 26 on which sutures may be attached to needles utilizing a pair of the clover leaf dies of the present invention. The apparatus 26 shown is manufactured and marketed as model 6A Suture Attaching Machine by B. G. Sulzle, Inc., Syracuse, N.Y. Other comparable machines suitable for attaching sutures may be utilized with the dies o the present invention.

The suture attaching machine 26 as illustrated in FIG. 6 includes table 27 having treadle 28 which is foot operated and connected via treadle rod 30 to suture press 32. The treadle 28 is mounted for pivotal movement on pivot rod 31.

Referring now to FIG. 7 there is shown a side view of the apparatus shown in FIG. 6. The suture press 32 is encircled and is shown in enlarged form in FIG. 7A. As can be seen in FIG. 7A, the pair of clover leaf dies 14 which are constructed according to the invention are positioned within the jaws of the suture press 32 and arranged to be stricken against a needle with the suture components in position as shown in FIG. 8.

Figure 8:
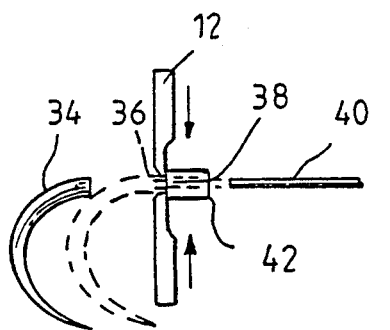
FIG. 8 is an exploded side view of a pair of clover leaf dies constructed according to the present invention positioned to attach a suture to a curved surgical needle.

The needle 34 shown in FIG. 8 is of a curved type having a straight rear end portion 36 which defines an elongated aperture 38 dimensioned for reception and attachment to an appropriately sized suture 40. The needle 34 is supported on a guide support 42 having a "V shaped" guide channel which positively determines and positions the needle location and orientation as shown. Thereafter, appropriate adjustments are made to predetermine the strike force to be transmitted to the needle and suture as may be appropriately calculated to obtain a predetermined pull-out force. The treadle is depressed to cause the dies to strike the needle.

It will be readily appreciated that the dies of the present invention are particularly advantageous in that all types of sutures may be readily attached to needles having an aperture in their blunt end, e.g., drilled end needles, utilizing a single strike force thereby avoiding the need to provide "double-hit" attachment as necessary with prior art dies. This procedure provides a suture having a needle which si symmetrical and unaffected by the distorting forces provided by dies and procedures of the prior art. Moreover, the single-hit attachment procedure provides consistent and controlled attachment of the suture and the needle which additionally reduces the time and effort to complete the attachment. Die life is increased; rejected needle/suture attachments are reduced; and attachment time is reduced. As a result the cost of producing a surgical suture is sizably reduced.

Example of comparisons of pull-out forces provided by the present invention ("Clover leaf" die) and prior art ("control") attachments are provided in the following table.

TABLE I

Clover Leaf Die vs. Controls
Size 0

| | Pull-Out Force | |
|---|---|---|
| | Pre-Steriliz | Post-Steriliz |
| Control 1 VICRYL brand SYNTHETIC absorbable suture (Prior Art Double-Hit) | (No Data) | n = 10  2.8 kgs |
| Control 2 Monofilament nylon suture (Prior Art Double-Hit) | n = 10  1.8 kgs | n = 10  1.8 kgs |
| Control 3 Braided synthetic absorbable suture (Prior Art Double-Hit) | n = 5  2.6 kgs | n = 5  2.9 kgs |
| Clover Leaf Die Braided synthetic absorbable suture | n = 15  3.5 kgs | n = 15  3.3 kgs |
| Clover Leaf Die Monofilament nylon suture | n = 15  2.9 kgs | n = 15  3.4 kgs |

The foregoing table clearly illustrates and underscores the effectiveness of the present invention in providing consistent and controlled needle/suture attachments using a single hit. In fact, in each case the attachments made according to the invention exhibited pull-out forces to separate the suture from the needle at least equal to those of the prior art double-hit (or multiple hit) attachments. In each instance the attachment of the present invention was accomplished by a single-hit procedure, in a fraction of the time, and provided a strike zone in the needle free of distortions or cold working effects. The last mentioned adverse effect can be expected with prior art needle-suture attachment methods.

The swaging dies of the present invention may be utilized with all types of needles such as curved needles, straight needles, or the like, provided they have an elongated aperture on their end portion for receiving the suture. Sutures usable with the present invention include silk, nylon, linen, cotton, polyester, polypropylene, stainless steel, natural materials such as catgut, synthetic polymers having glycolic acid ester linkages subject to hydrolytic degradation to non-toxic tissue compatible absorbable components, including polyglycolic acid. The sutures may be monofilamentary or braided, absorbable or non-absorbable. The dies of the present invention are preferably constructed of a hardened material such as tungsten carbide. However, it should be understood that all materials suitable for such die construction may be used, provided the geometric and configurational parameters taught by the present invention are met.

We claim:

1. A method of attaching a surgical needle having a generally cylindrical outer end portion and defining an elongated aperture having a generally circular cross-section, and a suture having a generally elongated end portion of generally circular cross-section corresponding in dimension to the elongated aperture of said needles, which comprises configuring a pair of dies such that each has a generally arcuate surface portion having generally inwardly extending crimping portions spaced by a plurality of concave portions, positioning an end portion of the suture within the aperture of the needle, positioning said pair of dies about the corresponding cylindrical portion of the needle with said surface portions facing the generally cylindrical outer end portion of the needle, applying inward force to said dies to displace said dies toward each other causing said dies to engage the needle so as to cause the generally arcuate surface portions of said dies to engage the surface portion of the needle to thereby cause crimping of the needle and reduction of the average dimension of the aperture defined thereby, whereby said concave portions define material relief zones to received and collect deformed material from the needle thereby avoiding distortion of the needle.

2. The method according to claim 1 wherein the step of configuring said pair of dies comprises configuring said arcuate surface portion so as to have continuous undulations defined by alternating convexities and concavities.

3. The method according to claim 2 wherein at least said portions of said dies defining said generally arcuate surface portion is comprised of hardened material.

4. The method according to claim 3 wherein said hardened material is at least one of tungsten carbide and high speed steel.

5. The method according to claim 4 wherein said needle is manufactured of stainless steel.

6. The method according to claim 5 wherein said suture is detachably attached to said needle whereby said suture may be readily separated from said needle by a sudden predetermined outward force provided by the user.

7. The method according to claim 5 wherein said suture is non-detachably attached to said needle whereby separation of said suture from said needle may be accomplished by cutting means.

8. The method according to claim 7 wherein the step of applying inward force to said dies to engage the needle is accomplished by a sudden inward impact force which moves the dies toward each other and the needle.

9. The method according to claim 2 wherein said undulations are defined by alternating convexities and concavities, said convexities each having its crest radially inward of a "mean" imaginary circle and said concavities each having its crest radially outward of said "mean" imaginary circle.

10. The method according to claim 9 wherein the radial distance between the crest of each convexity and said "mean" imaginary circle is substantially equal to the radial distance between the crest of each concavity and said "mean" circle.

11. The method according to claim 10 wherein said generally arcuate surface portion of each die intersects the die face at two end positions, the arcuate surface immediately adjacent each end portion being congruent with said "mean" imaginary circle.

12. A method of attaching a surgical needle having a generally arcuate outer end portion and defining an elongated aperture having a generally arcuate cross-section, and a suture having a generally elongated end portion of generally arcuate cross-section corresponding in dimension to the elongated aperture of said needle, which comprises configuring a pair of dies such that each has a generally arcuate surface portion having generally inwardly extending crimping portions spaced by a plurality of concave portions, said inward crimping portions being substantially equal to said concave portions, positioning an end portion of the suture within the aperture of the needle, positioning said pair of dies about the corresponding arcuate portion of the needle with said surface portions facing the generally cylindrical outer end portion of the needle, applying inward force to said dies to displace said dies toward each other causing said dies to engage the needle so as to cause the generally arcuate portions of said dies to engage the surface portion of the needle to thereby cause crimping of the needle and reduction of the average dimension of the aperture defined thereby, whereby said concave portions define material relief zones to receive and collect deformed material from the needle thereby avoiding distortion of the needle.

13. The method of attaching a surgical needle and a suture according to claim 12 wherein said step of applying inward force to said dies comprises applying force sufficient to substantially non-detachably attache the needle to said suture.

14. The method of attaching a surgical needle and a suture according to claim 13 wherein said step of applying inward force to said dies to engage the needle is accomplished by inward impact force which moves the dies toward each other and the needle.

15. The method of attaching a surgical needle and a suture according to claim 14 wherein said force is sufficient to substantially non-detachably attache the needle to said suture in accordance with the standards of the U.S. Pharmacopeia.

16. The method of attaching a surgical needle and a suture according to claim 12 wherein said step of applying inward force to said dies comprises applying force sufficient to substantially detachably attach the needle to said suture.

17. The method of attaching a surgical needle and a suture according to claim 16 wherein said step of applying inward force to said dies to engage the needle is accomplished by inward impact force which moves said dies toward each other and the needle.

18. The method of attaching a surgical needle and a suture according to claim 17 wherein said force is sufficient to substantially detachably attach the needle to said suture in accordance with the standards of the U.S. Pharmacopeia.

19. A method of attaching a surgical needle having a generally cylindrical outer end portion and defining an elongated aperture having a generally circular cross-section, and a suture having a generally elongated end portion of generally circular cross-section corresponding in dimension to the elongated aperture of said needle, which comprises configuring a pair of dies such that each has a generally arcuate surface portion having continuous undulations defined by alternating convexities and concavities, said convexities each having its crest radially inward of a mean imaginary circle and said concavities each having its crest radially outward of said means imaginary circle, positioning an end portion of the suture within the aperture of the needle, positioning said pair of dies about the corresponding cylindrical portion of the needle with said surface portion facing the generally cylindrical outer end portion of the needle, applying inward force to said dies to displace said dies toward each other causing said dies to engage the needle so as to cause the generally arcuate surface portions of said dies to engage the surface portion of the needle to thereby cause crimping of the needle and reduction of the average dimension of the aperture defined thereby, whereby said concave portions define material relief zones to receive and collect deformed material from the needle thereby avoiding distortion of the needle.

* * * * *